United States Patent
Seligman

[11] Patent Number: 6,151,400
[45] Date of Patent: Nov. 21, 2000

[54] AUTOMATIC SENSITIVITY CONTROL

[75] Inventor: Peter Seligman, Essendon, Australia

[73] Assignee: Cochlear Limited, Lane Cove, Australia

[21] Appl. No.: 08/817,686

[22] PCT Filed: Oct. 24, 1995

[86] PCT No.: PCT/AU95/00703

§ 371 Date: Apr. 23, 1997

§ 102(e) Date: Apr. 23, 1997

[87] PCT Pub. No.: WO96/13096

PCT Pub. Date: May 2, 1996

[30] Foreign Application Priority Data

Oct. 24, 1994 [AU] Australia ............................. PM9005

[51] Int. Cl.$^7$ ................................................. H04R 25/00
[52] U.S. Cl. ..................... 381/317; 381/318; 381/94.1;
    381/101; 381/106; 381/104; 381/107
[58] Field of Search ..................... 381/316, 317,
    381/318, 321, 320, 94.1, 94.3, 94.8, 101,
    93, 104, 106, 83, 71.14, 102, 107, 108

[56] References Cited

U.S. PATENT DOCUMENTS

| 4,052,678 | 10/1977 | Ramsland . | |
|---|---|---|---|
| 4,185,168 | 1/1980 | Graupe et al. | 381/318 |
| 4,405,831 | 9/1983 | Michelson | 381/321 |
| 4,630,304 | 12/1986 | Borth et al. . | |
| 4,718,099 | 1/1988 | Hotvet | 381/317 |
| 4,887,299 | 12/1989 | Cummins et al. . | |
| 4,996,712 | 2/1991 | Laurence | 381/104 |
| 5,144,675 | 9/1992 | Killion et al. | 381/317 |
| 5,329,243 | 7/1994 | Tay | 381/101 |
| 5,550,923 | 8/1996 | Hotvet | 381/103 |
| 5,701,352 | 12/1997 | Williamson, III | 381/104 |

FOREIGN PATENT DOCUMENTS

| 2 237463 | 5/1991 | United Kingdom . |
|---|---|---|
| WO 94/07305 | 3/1994 | WIPO . |

OTHER PUBLICATIONS

Abstract No. 93–276662/35, Anritsu Corp., Jul. 30, 1993.
Abstract No. 64–260631,Mitsubishi Electric Corp., May 24, 1991.

Primary Examiner—Curtis A. Kuntz
Assistant Examiner—Rexford N Barnie
Attorney, Agent, or Firm—Gottlieb Rackman & Reisman PC

[57] ABSTRACT

Again control arrangement for an auditory prosthesis, such as a hearing aid or cochlear prosthesis, is disclosed. The output of a controlled amplifier 11 is processed so as to derive an average noise floor level. This is compared to a predetermined level, and the gain adjusted slowly up or down in response to the comparison. Hardware and software implementations are disclosed.

31 Claims, 2 Drawing Sheets

AUTOMATIC SENSITIVITY CONTROL

TECHNICAL FIELD

The present invention relates to automatic gain control (AGC) systems for auditory prostheses and hearing aids, particularly but not exclusively for cochlear prostheses.

BACKGROUND

In devices involving the amplification of sound, or the provision of electrical stimuli so as to produce a sound percept, it is necessary to utilise an AGC system. This adjusts the gain utilised in an amplifier, so as to take account of the prevailing sound level in the vicinity. The use of a simple AGC which, say, always adjusts to a predefined level can give rise to difficulties where no meaningful sound is currently being produced—in this case, background noise may be amplified so as to become intrusive. In a conventional system with no manual gain control, this background noise will be amplified so as to have an average level equivalent to that of the sounds of interest, such as speech. This is clearly unsatisfactory for the user.

In most practical systems, a sensitivity or input gain control is provided to allow the maximum AGC gain to be varied by the user to an appropriate level. Patients will generally adjust this to a position which maximises the perceived signal to noise ratio. This will generally be where the AGC is just on the point of operating when another person is speaking to them. A higher setting than this means that the background noise level is raised by the AGC in the absence of speech whilst the signal amplitude is lowered when speech is present. This has the adverse effect that the background noise level appears to be higher, and will tend to influence adversely speech discrimination, as the signal amplitude information is compressed. If, on the other hand, the gain is set too low, the AGC will not operate at all and the signal may well be too soft to allow for good speech discrimination by the user.

Notwithstanding these difficulties, AGC is generally provided, as when the user himself speaks, the signal perceived by the microphone will be substantially louder than when another person speaks. Further, the person speaking may raise his or her voice. Without an AGC, either of these cases leads to limiting and distortion of the signal and corresponding degradation of output from the signal processor.

A further difficulty arises when a user moves from a quiet situation to a noisier one. In this situation, the noise floor is higher and the conversation louder. The AGC operates when other people and the user are speaking and the perceived signal to noise ratio is worse than the actual ratio because during speech the gain is lower than in the breaks. In this case, it would be advantageous to lower the sensitivity.

U.S. Pat. No. 4,718,099 to Hotvet discloses an AGC arrangement in which if an input signal exceeds a predetermined maximum, then a fast attack response acts to reduce gain. A variable release period is used. However, there is no disclosure of establishing a noise floor for the arrangement—an averaging arrangement is used. Another arrangement using a noise averaging and variable attack time approach is disclosed in U.S. Pat. No. 5,144,675 to Killion et al. Other disclosures use a combination of long and short term averaging, and a difference amplifier—for example U.S. Pat. No. 4,996,712 to Lawrence et al, and Australian patent application No 17099/88 by Hughes Aircraft Company.

It is an object of the present invention to provide an improved AGC system for hearing aids and auditory prostheses such that the sensitivity of the system responds better to the prevailing sound environment than previous devices.

SUMMARY OF THE INVENTION

According to one aspect, the present invention provides an automatic gain control system for an auditory system, comprising a controlled amplifier, characterised in that the maximum gain of the amplifier is varied in accordance with the prevailing noise floor.

Preferably, the output of the controlled amplifier is controlled using means for determining the average output noise floor, which is compared to a predetermined breakpoint. If the noise floor is above the breakpoint, the gain is slowly reduced—if it is below, the gain is slowly increased.

This arrangement is suitably employed in a hearing aid, cochlear prosthesis or other auditory prosthesis.

The advantage of this arrangement is that if the user moves into a noisier environment, the noise level will be reduced overall with a relatively slow response time, so that, for example, the AGC will not boost the gain up during breaks between speech so as to make the noise level louder than necessary.

BRIEF DESCRIPTION OF DRAWINGS

The present invention will be described in more detail with reference to the accompanying figures, in which.

DETAILED DESCRIPTION

Figure 1:
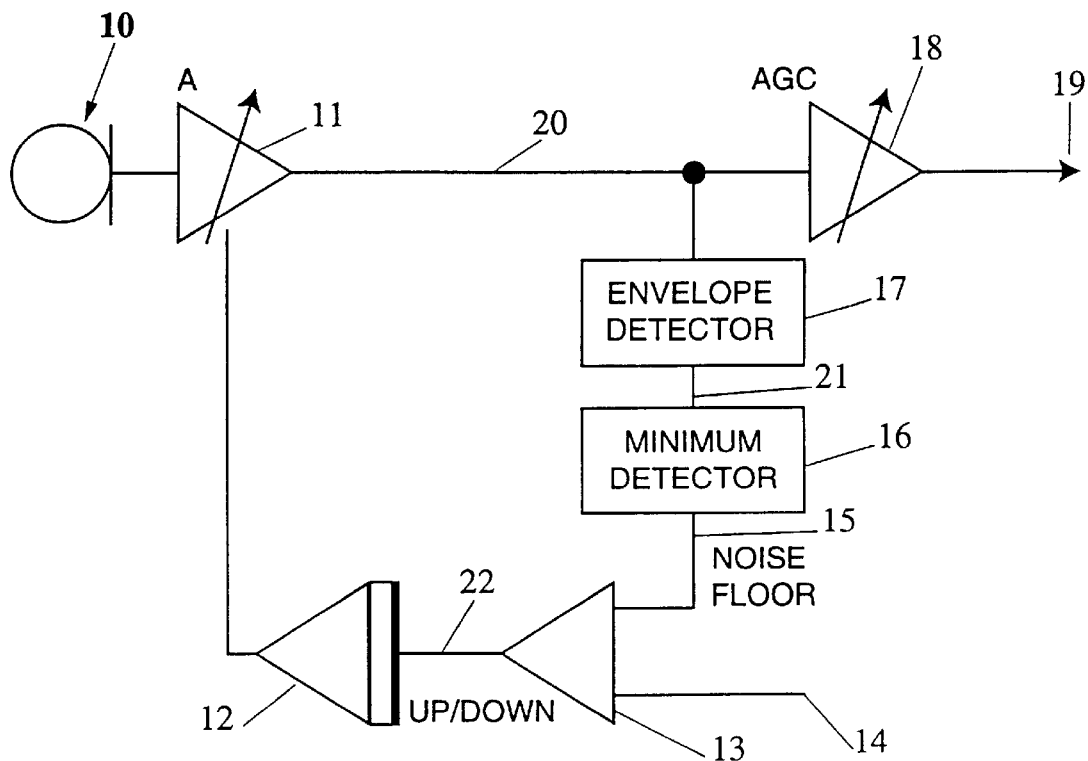
FIG. 1 which shows a schematic illustration of one implementation of the present invention.

Referring to FIG. 1, a signal is detected by microphone 10 and output to variable gain amplifier 11. The amplifier output 20 is processed by envelope detector 17 which rectifies signal 20 and removes the audio frequencies. The resulting envelope amplitude signal 21 is then processed by minimum detector 16, which responds rapidly to any reduction in envelope amplitude signal 21, and only gradually to increases. In this way, the output 15 of minimum detector 16 reflects the lowest signal amplitude over the preceding period. Typically, this period would be set by varying the time constants of the minimum detector to be several seconds. Thus, output 15 is the noise floor.

Comparator 13 compares signal 15 with a preset breakpoint value, which is determined so as to correspond to the highest acceptable level. If signal 15, that is, the noise floor, is above this level the comparator output signal 22 causes integrator 12 to start slowly ramping down. The reducing output signal from integrator 12 is fed back to control the gain of amplifier 11, and so the output signal 20 and consequently the noise floor signal 15 are decreased. If signal 15 is below the breakpoint, the comparator output signal 22 causes the integrator 12 to ramp up, and the gain of amplifier 11 is increased. In this way the maximum gain of the AGC is always kept down to a level such that the noise floor, in the absence of a signal, is close to the breakpoint.

Figure 2:
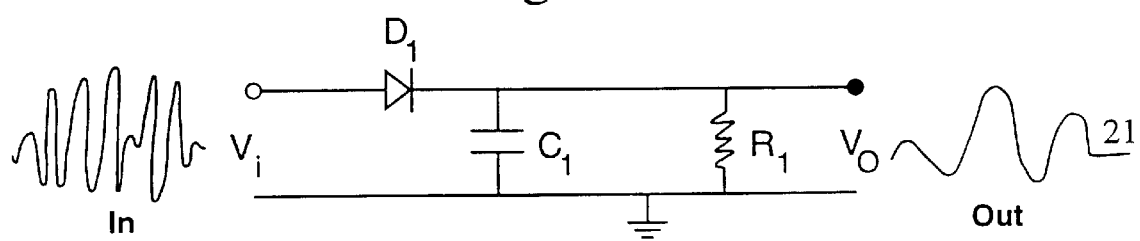
FIG. 2 illustrates schematically an implementation of the envelope detector.

Referring to FIG. 2, this shows a simple analog implementation of the envelope detector. This is a standard demodulation circuit, using diode D1 and filter R1C1. Preferably, R1C1 is much greater than 1/f, where f is the highest likely frequency in the audio signal.

Figure 3:
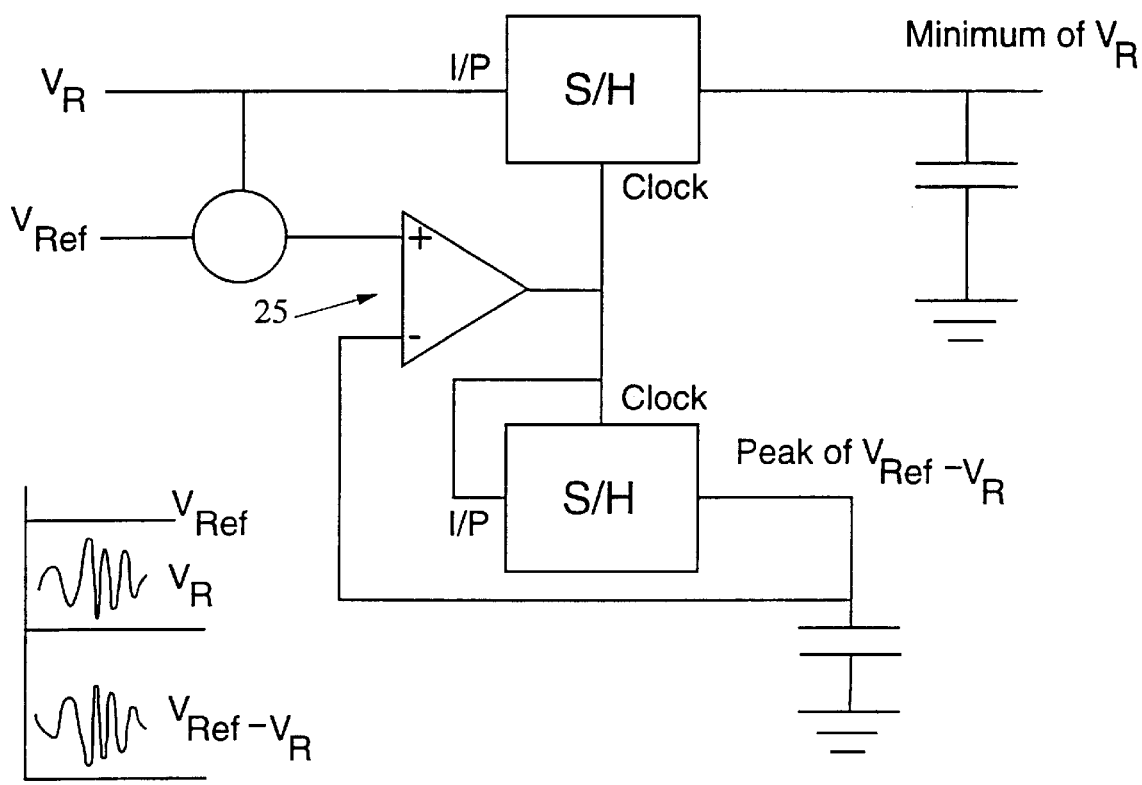
FIG. 3 illustrates schematically an implementation of the minimum detector.

FIG. 3 illustrates a possible minimum or dip detector arrangement, implemented in hardware. This implementation changes the problem of finding the minimum of the envelope detector output signal $V_R$, to that of finding the peak of $V_{Ref}-V_R$, where $V_{Ref}$ is a reference voltage. Operational amplifier 25 is configured in difference mode, so as to detect $V_{Ref}-V_R$, and accordingly output a minimum value for $V_R$.

Figure 4:
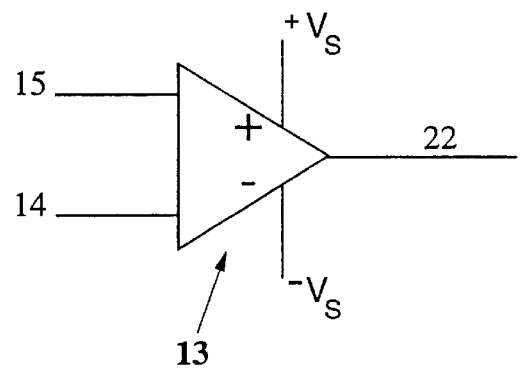
FIG. 4 illustrates schematically an implementation of the comparator.

FIG. 4 illustrates the comparator, using op-amp 13 to compare noise floor 15 to the predetermined breakpoint 14.

Figure 5:
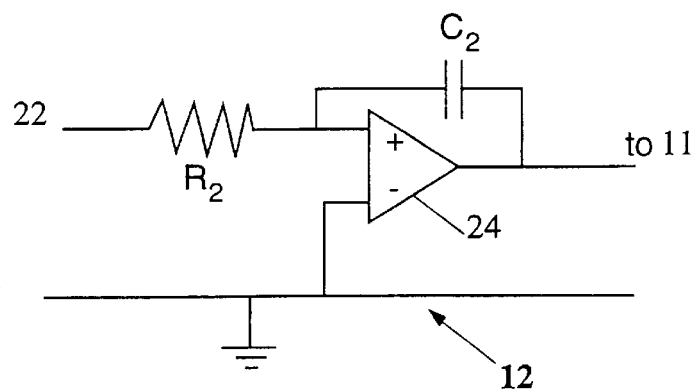
FIG. 5 illustrates schematically an implementation of the integrator.

FIG. 5 illustrates a hardware implementation of the integrator. Op amp 24 is feedback controlled by capacitor C2 and resistor R2 If comparator output 22 is high, indicating that the detected noise floor is greater than the breakpoint, then Op amp 24 will ramp down, thereby reducing the output of amplifier 11. If the output 22 is low, then op amp will ramp up, so as to increase output from the amplifier.

The present invention may be implemented wholly or partly in software. In one implementation, the signal for which gain control is required is passed through analog to digital converter of conventional type with a sample rate of 16.026 kHz. The input voltage range is 366 $\mu$V to 1.5 V peak to peak. Each decrement step in the gain is 8 times the size of each increment step. Following is a pseudo code description of one software implementation.

Start ASC:
  Get new input sample (A1)
  % Amplify input signal A2=Gain*A1
  % Calculate the signal envelope and find minima (background noise in % absence of speech)
  Envelope=average of (A2 over 64 ms)
  Noise_Floor=Minimum (values of Envelope over last 10 seconds)
  % Update Gain to Direct Envelope minima towards Breakpoint
  If (Noise_Floor<Breakpoint) then increment (Gain) else Decrement (Gain)
  % Limit Gain to sensible range
  If (Gain>GainMax) then Gain=GainMax
  If (Gain<GainMin) then Gain=GainMin
  GOTO Start ASC In this way, the functions of envelope detection, minimum detection, comparator and integrator are performed in software, and provide gain control signals for the amplifier.

There are many alternative methods of implementation of this invention. In the context of cochlear implants, the present invention may be incorporated within the speech processing devices manufactured by the present applicant. In the SPECTRA and MSP devices, the present invention may be implemented using an attenuator formed by a FET used as variable resistance to form an attenuator, in combination with software in the encoder. Alternatively, a digital attenuator may be used, together with a hardware implementation using up/down counters and digital comparators. Other implementations are also possible, such as totally digital or totally analog. A totally digital approach would require an analog to digital converter at the front end, with the attenuation performed within a digital signal processor. A totally analog approach would use operational amplifiers, comparators and integrators to achieve the same results.

Other hybrid approaches different to those described in this document are also possible and obvious to anyone skilled in the art. It will be appreciated that the precise hardware arrangement disclosed is only one possible embodiment. Variations and additions within the general concept will be apparent to the reader.

What is claimed is:

1. A method for processing in an auditory prosthesis an audio signal to optimize the intelligibility of an output of said auditory prosthesis as perceived by a user of said auditory prosthesis, comprising the steps of:
   a) amplifying said audio signal by means of a gain adjustable amplifier to produce a gain adjusted audio signal;
   b) determining an average noise floor of said audio signal wherein said average noise floor is indicative of the lowest noise level within a predetermined period;
   c) adjusting the gain of said gain adjustable amplifier by means of a feedback control arrangement responsive to said gain adjusted audio signal and said average noise floor; and
   d) conveying said gain adjusted audio signal to the remainder of said auditory prosthesis for further processing.

2. A method according to claim 1, wherein the step of adjusting the gain of said gain adjustable amplifier by means of a feedback control arrangement responsive to said gain adjusted audio signal comprises the further steps of:
   a) extracting the envelope of said gain adjusted audio signal to produce an envelope signal;
   b) monitoring said envelope signal to produce a noise floor signal indicative of said envelope signal's minimum value during a period of time;
   c) comparing said noise floor signal with a breakpoint set by said auditory prosthesis user; and
   d) decreasing the gain of said gain adjustable amplifier if said noise floor signal is greater than said breakpoint set by said user of said auditory prosthesis or increasing the gain of said gain adjustable amplifier if said noise floor signal is less than said breakpoint set by said user of said auditory prosthesis.

3. A method according to claim 2, wherein the step of extracting the envelope of said gain adjusted audio signal to produce said envelope signal is accomplished by means of a diode detector circuit.

4. A method according to claim 3, wherein the step of monitoring said envelope signal to produce a signal indicative of the minimum value of said envelope signal during said period of time is implemented by means of a dip detector.

5. A method according to claim 1, wherein the gain of said gain adjustable amplifier is increased relatively slowly in response to a decrease in said average noise floor and is decreased relatively rapidly in response to an increase in said average noise floor.

6. A method according to claim 1, wherein said auditory prosthesis is a hearing aid.

7. A method according to claim 1, wherein said auditory prosthesis is a cochlear prosthesis.

8. A method for processing a digital audio signal in an auditory prosthesis by means of a microprocessor and software in order to maximize the intelligibility of sounds delivered to a user, comprising the steps of:
   a) performing computations on said digital audio signal to apply gain to said digital audio signal thereby generating a gain adjusted digital audio signal wherein the degree of gain applied is subject to increment or decrement;

b) performing computations on said gain adjusted digital audio signal to produce a digital envelope signal;

c) performing computations on said digital envelope signal to generate a noise floor value characteristic of a minimum of said digital envelope signal during a preset period of time;

d) comparing said minimum of said digital envelope signal with a breakpoint value set by a user; and e) increasing the gain applied to said digital audio signal if said noise floor value is less than said breakpoint value or decreasing the gain applied to said digital audio signal if said noise floor value is greater than said breakpoint value.

9. A method according to claim 8, wherein said computations performed on said digital audio signal to apply gain to said digital audio signal increase the gain relatively slowly in response to a decrease in said noise floor value and decrease the gain relatively rapidly in response to an increase in said noise floor value.

10. A method according to claim 8, wherein said auditory prosthesis is a hearing aid.

11. A method according to claim 8, wherein said auditory prosthesis is a cochlear prosthesis.

12. An apparatus for processing in an auditory prosthesis an audio signal which includes a noise component to optimize the intelligibility of the output of said auditory prosthesis as perceived by a user of said auditory prostheses, comprising:

a) a gain adjustable amplifier to operatively amplify said audio signal thereby producing a gain adjusted audio signal;

b) a feedback control arrangement responsive to said gain adjusted audio signal to operatively adjust the gain of said gain adjustable amplifier, including:

means for determining an average noise floor of said gain adjusted audio signal, said average noise floor corresponding to the lowest level of said noise component; and means for providing a control signal to said gain adjustable amplifier so as to vary the gain of said gain adjustable amplifier; and c) means for conveying said gain adjusted audio signal to the remainder of said auditory prosthesis for further processing.

13. An apparatus according to claim 12, wherein said feedback control arrangement responsive to said gain adjusted audio signal, comprises:

a) means for extracting the envelope of said gain adjusted audio signal to produce an envelope signal;

b) means for monitoring said envelope signal to produce a noise floor signal indicative of said envelope signal's minimum value during a period of time;

c) means for comparing said noise floor signal with a breakpoint set by said auditory prosthesis user;

d) means for decreasing the gain of said gain adjustable amplifier if said noise floor signal is greater than said breakpoint set by said user of said auditory prosthesis; and e) means for increasing the gain of said gain adjustable amplifier if said noise floor signal is less than said breakpoint set by said user of said auditory prosthesis.

14. An apparatus according to claim 13, wherein said means for extracting the envelope of said gain adjusted audio signal to produce said envelope signal is accomplished by means of a diode detector circuit.

15. An apparatus according to claim 14, wherein said means for monitoring said envelope signal to produce a signal indicative of the minimum value of said envelope signal during said period of time is implemented by means of a dip detector.

16. An apparatus according to claim 12, wherein said gain adjustable amplifier comprises a voltage controlled amplifier.

17. An apparatus according to claim 12, wherein said gain adjustable amplifier comprises a fixed gain stage and a variable attenuation stage.

18. An apparatus according to claim 17, wherein said variable attenuation stage is implemented by means of a field effect transistor.

19. An apparatus in accordance with claim 12 wherein said feedback control arrangement further includes means for comparing said average noise floor to a predetermined level; and wherein said means for providing a control signal is responsive to said means for comparing by increasing said gain when said noise floor is below said predetermined level and by decreasing said gain when said noise floor is above said predetermined level.

20. An apparatus according to claim 12, wherein said means for providing said control signal to said gain adjustable amplifier comprises an integrator.

21. An apparatus according to claim 12, wherein the gain of said gain adjustable amplifier is increased relatively slowly in response to a decrease in said average noise floor and is decreased relatively rapidly in response to an increase in said average noise floor.

22. An apparatus according to claim 12, wherein said auditory prosthesis is a hearing aid.

23. An apparatus according to claim 12, wherein said auditory prosthesis is a cochlear prosthesis.

24. An apparatus for processing a digital audio signal in an auditory prosthesis by means of a microprocessor and software in order to maximize the intelligibility of sounds delivered to a user, said software containing instructions comprising the steps of:

a) performing computations on said digital audio signal to apply gain to said digital audio signal thereby generating a gain adjusted digital audio signal wherein the degree of gain applied is subject to increment or decrement;

b) performing computations on said gain adjusted digital audio signal to produce a digital envelope signal;

c) performing computations on said digital envelope signal to generate a noise floor value characteristic of a minimum of said digital envelope signal during a preset period of time;

d) comparing said minimum of said digital envelope signal with a breakpoint value set by said user; and e) increasing the gain applied to said digital audio signal if said noise floor value is less than said breakpoint value or decreasing the gain applied to said digital audio signal if said noise floor value is greater than said breakpoint value.

25. An apparatus according to claim 24, wherein said computations performed on said digital audio signal to apply gain to said digital audio signal increases said gain relatively slowly in response to a decrease in said noise floor value and decreases said gain relatively rapidly in response to an increase in said noise floor value.

26. An apparatus according to claim 24, wherein said auditory prosthesis is a hearing aid.

27. An apparatus according to claim 24, wherein said auditory prosthesis is a cochlear prosthesis.

28. An apparatus according to claim 19, wherein said mean for comparing said average noise floor to said predefined level comprises an operational amplifier.

29. An apparatus for processing in an auditory prosthesis an audio signal having a noise component to optimize the intelligibility of the output of said auditory prosthesis as perceived by a user of said auditory prosthesis, comprising:

an amplifier having a variable gain controlled by a gain control signal, said amplifier receiving said audio signal and producing in response a gain adjusted audio signal;

a noise floor detector receiving said audio signal and being constructed to detect a noise floor of said noise component by determining the lowest level of said noise component over a predetermined time period;

a gain control circuit coupled to said noise floor detector and generating said gain control signal responsive to said noise floor; and an output terminal transmitting said gain adjusted audio signal for perception by the user.

30. The apparatus of claim 29 wherein said gain control circuit includes a comparator coupled to said noise floor detector, said comparator being constructed to compare said noise floor to a predetermined value and to increase the gain of said amplifier if said noise floor is below said predetermined value and to decrease said gain if said noise floor is above said predetermined value.

31. The apparatus of claim 29 wherein said noise floor detector includes an envelope detector arranged to receive said audio signal and to detect an envelope of said audio signal, and a minima detector for detecting a minimum value of said envelope, said minimum value corresponding to said noise floor.

\* \* \* \* \*